United States Patent [19]
De Wit et al.

[11] Patent Number: 6,042,788
[45] Date of Patent: Mar. 28, 2000

[54] CHEMICALLY SENSITIVE SENSOR COMPRISING ARYLENE ALKENYLENE OLIGOMERS

[75] Inventors: Michael De Wit, Sint-Amands; Emmanuel Vanneste, Wilrijk; Frank Blockhuys, Berchem; Gunter Verreyt, Mol; Wim Tachelet, Burcht; Luc J. Nagels, Mechelen; Herman J. Geise, Antwerpen, all of Belgium

[73] Assignee: Interuniversitair Micro-Elektronica Centrum (IMEC), Leuven, Belgium

[21] Appl. No.: 08/985,806

[22] Filed: Dec. 5, 1997

[30] Foreign Application Priority Data

May 30, 1997 [EP] European Pat. Off. ............. 97870082
May 15, 1997 [EP] European Pat. Off. ............. 97870068

[51] Int. Cl.[7] .................................................. G01N 27/12
[52] U.S. Cl. ........................... 422/82.02; 422/90; 422/98
[58] Field of Search ................ 422/58, 68.1, 69, 422/70, 82.01, 82.02, 83, 88, 89, 90, 93, 98

[56] References Cited

U.S. PATENT DOCUMENTS

| | | | |
|---|---|---|---|
| 4,907,441 | 3/1990 | Shurmer | 73/23 |
| 5,512,490 | 4/1996 | Walt et al. | 436/171 |
| 5,571,401 | 11/1996 | Lewis et al. | 205/787 |
| 5,674,752 | 10/1997 | Buckley et al. | 436/151 |
| 5,675,070 | 10/1997 | Gelperin | 73/23.34 |
| 5,698,089 | 12/1997 | Lewis et al. | 205/787 |
| 5,766,952 | 6/1998 | Mann et al. | 436/2 |
| 5,788,833 | 8/1998 | Lewis et al. | 205/787 |

OTHER PUBLICATIONS

Diaz, A.F.; Crowley, J.; Bargon, J.; Gardini, G.P.; and Torrance, J.B. "Electrooxidation of Aromatic Oligomers and Conducting Polymers." J. Electroanal. Chem. 121(1981), 355–361.

Kossmehl, Gerhard; Samandari, Massoud Polyarylenealkenylenes and Polyheteroarylenealkenylenes, 17 Syntheses of Alkoxylated Poly(2–nitro–1,4–phenylenevinylene–1, 4–phenylenevinylene)s and poly(2,5–dimethoxy–1, 4–phenylenevinylene–14–phenylenevinylene)2 a, 1985.

Josowicz, M and Janata, J. "Suspended Gate Field Effect Transistor Modified with Polypyrrole as Alcohol Sensor." Anal. Chem. (1986), 58, 514–517.

Yang, Z.; Geise, H. J. "Electrical conductivity of iodine–doped poly(para–phenylene vinylene) model compounds blended with polystyrene." Synth. Met. (1992), 47(1), 95–104.

Mates, T. E.; and Ober, C. K. "Conductivity and Third–d–Order Nonliner Optical Measurements of Polymers with Distrylbenzene and Diphenyrllbutadiene Segments." (1993), 5, 217–221, 1993.

E. Staes, L.J. Nagels, G. Verreyt, S. Jacobs, Y. Bao, H.J. Greise, Electroanalysis 9(1997) 1197.

*Primary Examiner*—Jeffrey Snay
*Attorney, Agent, or Firm*—Knobbe, Martens, Olson & Bear, LLP

[57] ABSTRACT

Chemically sensitive sensors, suitable for detecting analytes in fluids (in gaseous or liquid phase), characterised in that the chemically sensitive sensors comprise a chemically sensitive probe, which comprises one or a blend of several arylene alkenylene oligomers.

23 Claims, 9 Drawing Sheets

CHEMICALLY SENSITIVE SENSOR COMPRISING ARYLENE ALKENYLENE OLIGOMERS

FIELD OF THE INVENTION

The invention is situated in the domain of chemical sensors for the analytic characterization of gases and liquids.

The invention concerns the use of semi-conductive coatings, based on doped π-conjugated arylene alkenylene oligomers, in the active layer of sensors, and in arrays of such sensors applicable for the analytical characterization of gases and liquids, applicable in detecting systems for chromatography as well as in the context of an "electronic nose" or "electronic tongue".

BACKGROUND OF THE INVENTION

High-performance liquid chromatography (HPLC) is an analytical quantification and detection method in which an eluent is forced through a packed column. The mixture containing the product that has to be detected or quantified is submitted to an eluent flow. Since different products have different elution speeds, the products are separated from each other at the end of the column. After being separated on the column, the product is detected in a flow-through detector. The detector response can be translated into the concentration of the product.

Similarly, in gas chromatography, detectors are used to quantify or detect analytes in a gaseous mixture. Detectors that can be used for these purposes can be the usual electrochemical detectors (ECD). The operation principles of ECD's are well described.

ECD's operate on the basis of potentiometric, amperometric and conductimetric phenomena. The present state of the art will be reviewed for such systems.

Potentiometric detectors are widely used in analytic chemistry, the best known example being the pH- meter. The operating principles are well known. Such detectors are often specific for one ion (ion-selective electrodes). In chromatographic systems (and other systems, based on hydrodynamic measurements) however, potentiometric detection is still poorly developed. For these applications one needs sensors with low specificity, in contrast to batch techniques in which high specificity is required.

The kind of electrodes that are mostly used currently are metal electrodes (copper), so-called liquid-membrane ion-selective electrodes, $Ag^+/AgCl$ electrodes, and anion-exchange membranes (Potentiometrische detektie van anionen in LC en CE met polymere vloeibaar-membraan elektroden, B. De Backer, Universitaire Instelling Antwerpen, 1995). Such potentiometric sensors are not yet commercially available for liquid chromatographic systems. This is due to the low sensitivity, the slow response and the sometimes irreversible behavior of the sensors under chromatographic conditions.

Liquid membrane electrodes work well under chromatographic conditions as well as in Capillary Zone Electrophoretic (CZE) separations (Grate, M. H. Abraham, Sensors and Actuators B, 3 (1991), 85).

In HPLC one usually uses glassy carbon as the active material in amperometric detectors. Glassy carbon made amperometric detection in HPLC a success in the last 20 years. A wide range of products can be detected with this material. Yet, many chemical compounds can in practice not be oxidized or reduced on the surface of glassy carbon, because of the low reaction rates. Each year about 100 publications report about efforts to modify glassy carbon while improving the kinetics of the oxidation and reduction processes. So far, no significant improvements were made. Another material successfully used in amperometric HPLC detection is polycrystalline platinum, used in the so-called "Pulsed amperometric detection" (PAD) of carbohydrates. Recently, much research is carried out on enzyme-electrodes. The enzymes, immobilized on the electrodes, act as catalysts in the electron transfer from the analyte to the electrode underneath.

Glassy carbon is chemically inert, thereby making developments such as electrode derivatisation or enzyme coupling difficult.

A different application for chemical sensors is in the context of an electronic nose. An electronic nose is an instrument in which an array of sensors, each of which have partial selectivity, is used in combination with a pattern recognition system, and which can be used to recognize simple and/or complex aromas and gas mixtures. Such an array of sensors is described in U.S. Pat. No. 5,571,401.

The electronic nose can be employed in a wide range of applications, for example in industry, medicine, environmental protection, distribution and transport as well as in forensic investigations. In the food and beverage industry one may apply a chemical nose to monitor the freshness, to control quality of the starting, and the middle, and the final products as well as to monitor fermentation processes.

The advantage is that the quasi on-line (in situ) monitoring of the aroma (odor) may lead to an automated control system. Identification and/or quality control of starting products are potential applications in the chemical and pharmaceutical industry, because the "nose" offers a fast and universal analytical method. In medicine, the nose can be used in breath analyses. The patient's breath allows the diagnosis of some diseases, for example the odor of acetone is an indication for diabetes. The odor pattern may be helpful to identify the source of industrial emissions. Yet another potential use is a fast risk analysis in the event of road accidents involving chemicals.

On the spot determinations of fire accelerators may be another application. This list of possible applications is not complete, and other applications will appear. It shows, nevertheless, that the development of the electronic nose is important with many advantageous applications. In several of these applications, a small response time is needed.

The nose must be able—after a learning stage—to distinguish between the aromas of two or more mixtures, each containing a multitude of components. The sensors must operate on a molecular level. Furthermore, a sensor in an electronic nose must have partial selectivities to a wide spectrum of gases, rather than a high sensitivity to only one particular gas. Most existing gas sensors lack the wide spectrum of sensitivities to a variety of gases. Sensors based on metal oxide semi-conductors (MOS) Type 1 sensors, are widely and successfully employed in the sensor industry. Yet in the context of a chemical nose they are inferior compared to other materials. Particularly the number of different MOS materials that can be produced by inorganic synthesis, is very small compared to variability offered in products through organic synthesis.

Other types of sensors considered for application in an electronic nose are all based on the partial, selective permeability of polymers for gasses. On this single physical phenomenon, many technologies can be grafted, such as electrochemical sensors. Also, one knows surface acoustic wave and quartz crystal microbalance sensors using polymer coatings (Dickinson, J. White, J. S. Kauer, D. R. Walt, Nature, 382 (1996), 697) (type 2 sensors). Type 3 sensors exist, based on the fluorescent properties of optical fibers with a polymer coating. Type 4 sensors are conductimetric sensors based on conventional polymers where conductivity is introduced by mixing graphite particles with the polymer.

Conductimetric gas sensors based on conducting polymers form a group of sensors (type 5) that are important in the context of the electronic nose (Persaud, G. Dodd, Nature, 229 (1982), 352). Conducting polymers consist of a long sequence of alternating single and double bonds. This π-conjugated system can be made conductive via oxidation or reduction in a process called doping. The conductivity is influenced by the environment. In other words, conductivity changes upon contact with different vapours. These compounds are well suited for implementation in a chemical nose.

The use of polypyrrole, polyaniline, poly-N-methylpyrrole and poly-5-carboxyindole has been reported. (P. N. Bartlett, S. K. Ling-Chung, Sensors and Actuators, 20, (1989), 287). More type 5 sensors have been made by variation of functional groups on the main skeleton or by a variation of doping materials.

At this moment in time 5 companies offer commercial versions of an electronic nose. They are
(1) Aromascan plc., Electra House, Electra Way, CREWE CW1 1WZ, UK (offering a nose based solely on conducting polymers);
(2) Neotronics, Western House 2, Cambridge Road, Stansted Mountfitchet, Essex CM24 8BZ, UK (offering a nose containing conducting polymer and MOS sensors);
(3) AlphaMOS s.a., 3 Avenue Didier Durat, 31400 Toulouse, France (offering a nose solely based on MOS sensors);
(4) Nordic Sensor Technologies AB, Teknikringen 8, S-583 30 Link'ping, Sweden (offering a nose based on MOS sensors) and
(5) Lennartz Electronic, Bismarckstrasse 136, D-72072 Thbingen, Germany (offering a nose based on MOS and quartz crystal microbalance sensors).
Other references to this subject are:
ref. 1: New Scientist, Feb. 18, 1993.
ref. 2: C&EN, Aug. 13, 1996.
ref. 3: Bartlett, J. W. Gardner, "Sensors and Sensory Systems for an Electronic Nose", Kluwer Academic Publisher, Dordrecht, 1992.
ref. 4: Stetter et al., "Sensor systems for an electronic nose.", Kluwer Academic Publischer, Dordrecht, 1992).
ref. 5: Mills, F. Walsh, I. Whyte, Chemical Technology Europe, Jul.–Aug. 26, 1996,
ref. 6: "Selective sample handling and detection in high-performance liquid chromatography", Journal of Chromatography Library, vol. 39A, R. W. Frei and K. Zech, Ed., Elsevier, Amsterdam 1981.
ref. 7: "Principles of ion-selective electrodes and membrane transport", W. E. Morf, Ed., Elsevier, Amsterdam 1981.

SUMMARY OF THE INVENTION

This invention regards chemically sensitive sensors, suitable for detecting analytes in fluids (in gaseous or liquid phase), characterised in that the chemically sensitive sensors comprise a chemically sensitive probe which comprises one or a blend of several arylene alkenylene oligomers. The arylene alkenylane determines at least one response signal. The invention further comprises means for converting the response signal to a sensor response.

These oligomers can also be mixed with polymers. Doping is preferred to obtain workable resistances. Sensors according to the invention are applicable in a chromatography apparatus such as a GC (gas chromatograph) or HPLC (High Performance Liquid Chromatography) for detecting analytes. The possibility to use different arylene alkenylene oligomers for different sensors, which results in a different selectivity and sensitivity of said sensors for a given analyte, makes the sensors according to the invention very suitable for arrays of sensors. Combined with a pattern recognition system, such arrays of sensors are configurable as an electronic nose or tongue.

We recall that the electronic nose consists of a pattern recognition system in combination with a sensor array.

In analogy to the electronic nose, an electronic tongue can be developed: it would be an apparatus consisting of an array of sensors capable of characterizing the composition of a liquid. Again a number of sensor types come into consideration among which sensors based on conducting oligomers.

Other systems that require several sensors with different responses can also be developed using sensors according to the present invention.

The response signal can be determined by the interaction of the oligomer with the analyte or the fluid.

DETAILED DESCRIPTION OF THE INVENTION

Figure 1:
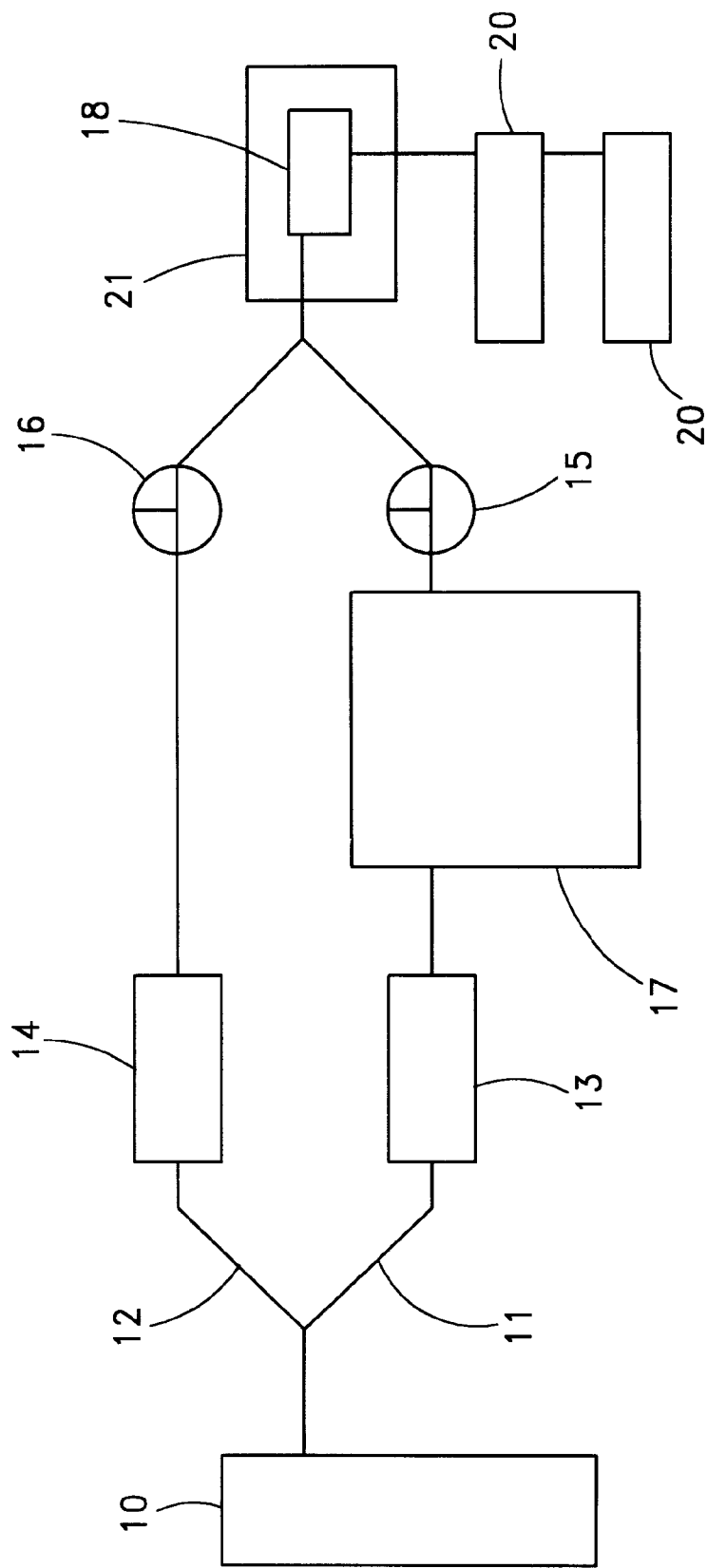
FIG. 1 describes the experimental setup for the examples 1 to 4.

A chemically sensitive sensor for the detection of an analyte in a fluid is described in the invention, said chemically sensitive sensor comprising a chemically sensitive probe which comprises one or several arylene alkenylene oligomers. Said fluid can be a liquid, a gas or a vapour. Said probe can be applied as a coating on a carrier surface and can be a probe. Said chemically sensitive sensor can further comprise electrodes able to put a voltage over said chemically sensitive probe. The probe can be a resistor or a coating or another structure.

The chemical structure of arylene alkenylene oligomers can be defined as follows: every possible sequence of one or more aromatic or heteroaromatic units like benzene, thiophene, pyrrole, aniline, indole, and many others (the arylene segments) which can be connected by one or more alkenyl segments ($-(CR=CR'-)_n$). The backbone can be substituted as well on the aryl segments as on the alkenyl segments. The type of substituents have an effect on the partial selectivity of the coatings, the solubility of the oligomers, their oxidation potential and the nominal electrical conductivity. The substituents can be methyl(Me), ethyl(Et), propyl(Pr), butyl(Bu), isobutyl(iBu), methoxy (MeO), ethoxy(EtO), propoxy(PrO), butoxy(BuO), isobutoxy(iBuO) Pentoxy (PtO), isopentoxy (IPtO), hexoxy (HxO), heptoxy (HpO), octoxy (OcO), hexadecoxy (HdO), (or any other alkyl or alkoxy residue), —CHO, —CN, —COOH, —$C_6H_5$, anthracene and naphthalene, —$CH_2X$, —X (with X=F, Cl, Br,I), and all other substituents. The chain length of these arylene alkenylene oligomers can be best expressed in the number of separate arylene segments in the molecule. The length of the oligomers for this invention ranger from 2 to 20 coupled segments. Most of the oligomers mentioned in the examples and the following listing are synthesized via the Wittig route. Other synthetic routes such as the Knoevenagel condensation, the McMurry and the Grignard coupling are also possible.

The here described conductive materials perform better than the classic materials. They react fast and reversibly on analyte concentrations and show high sensitivity. The materials are easy to coat, to give mechanically stable coatings, which can be used under chromatographic conditions for months, without a significant deterioration of performance.

For the purpose of simplification a system of short notations will be used rather than the IUPAC nomenclature. The letters F for a 2- or 2,5-substituted furane-ring, B for a 1- or 1,4-substituted benzene, S for a 2- or 2,5-substituted thiophene, N for a 2- or 2,5-substituted pyrrole, Naf for naphthalene, Ant for anthracene and BiT for bithienyl will be used. If not further specified 2,5- coupled hetero aromates and para-coupled benzenes are meant. A simple ethenylic segment is not mentioned unless it is substituted. If substituted the notation is (2( )) with the position of the substituents and the type of substituent between brackets. Analogously a 1,4- butadienylic segment is indicated by (4). Substituents at the end of the molecule are always explicitly mentioned and an end-standing hydrogen atom is symbolized by (-)

A few examples of the shortened notation in relation with the full name are given next:
1,4-bis(2-[3,4,5-trimethoxyphenyl]ethenyl)-2,5-dimethoxybenzene is equal to
(3,4,5 triMeO)BB(2,5diMeO)B(3,4,5 triMeO);
1,4-bis(2-[3,4,5-trimethoxyphenyl]ethenyl) benzene is equal to (3,4,5 triMeO)BBB(3,4,5 triMeO);
1,4-bis(2-[3,4,5-trimethoxyphenyl]ethenyl)-2,5-dimethylbenzene is equal to (3,4,5 triMeO)BB(2,5 diMe)B(3,4,5 triMeO);
1,4-bis(2-[3,4,5-trimethoxyphenyl]ethenyl)-2,5-diethoxybenzene is equal to (3,4,5 triMeO)BB(2,5 diEtO)B(3,4,5 triMeO);
1,4-bis(2-[3,4,5-trimethoxyphenyl]ethenyl)-2,5-dipropoxybenzene is equal to (3,4,5 triMeO)BB(2,5 diPrO)B(3,4,5 triMeO);
1,4-bis(2-[3,4,5-trimethoxyphenyl]ethenyl)-2,5-dibutoxybenzene is equal to (3,4,5 triMeO)BB(2,5 diBuO)B(3,4,5 triMeO);
1,4-bis(2-[3,4,5-trimethoxyphenyl]ethenyl)-2,5-dihexoxybenzene is equal to (3,4,5 triMeO)BB(2,5 diHxO)B(3,4,5 triMeO);
2,5-bis(2-[4-methoxyphenyl]ethenyl)thiophene is equal to (MeO)BTB(MeO);
2,5-bis(2-[3,4,5-trimethoxyphenyl]ethenyl)thiophene is equal to (3,4,5 triMeO)BTB(3,4,5 triMeO);
1,4-bis(2-[N-methyl-2-pyrryl]ethenyl)-2,5-dibutoxybenzene is equal to (N-methyl)NB(2,5 diOBuO) N(N-methyl).

Using this notation, a division of these oligomers in a number of classes can be done and a few examples of the named classes are given next:

Class BB:
—BB—, (2,5diMeBr)B(2,5 diMeBr), MeBBMe, MeBAnt, (MeO)BB(MeO), (EtO)BB(EtO), (PrO)BB (PrO), (BuO)BB(BuO), (iBuO)BB(iBuO), (PtO)BB (PtO), (iPtO)BB(iPtO), (HxO)BB(HxO), (HpO)BB (HpO), (OcO)BB(OcO), (HdO)BB(HdO), (OHC)BB (CHO), —BB(2,3,4 triMeO), MeBB(2,3,4 triMeO), ($BrCH_2$)BB($NO_2$) ClBB($NO_2$).

Class BBB:
—BBB—, —B(2(2-phenyl))B(2(2-phenyl))B—, —BB (2,5 diEtO)B—, —BB(2,5-diPrO)B—, —BB(2,5-diBuO)B—, MeBBBMe, MeB(2(1-phenyl))B(2(1-phenyl))BMe, AntB(2,5 diMe)Ant, (MeO)BBB(MeO), (EtO)BBB(EtO), (PrO)BBB(PrO), (BuO)BBB(BuO), (iBuO)BBB(iBuO), (PtO)BBB(PtO), (iPtO)BBB (iPtO), (HxO)BBB(HxO), (HpO)BBB(HpO), (OcO) BBB(OcO), (HdO)BBB(HdO), (3,4,5-triMeO)BBB(3, 4,5-triMeO), (3,4,5-triMeO)B(2(2-CN))B(2(2-CN))B (3,4,5-triMeO), (3,4,5-triMeO)BB(2,5-diMeO)B(3,4, 5-triMeO), (3,4,5-triMeO)BB(2,5-diEtO)B(3,4,5-triMeO), (3,4,5-triMeO)BB(2,5-diPrO)B(3,4,5-triMeO), (3,4,5-triMeO)BB(2,5-diBuO)B(3,4,5-triMeO), (2,4,6-triMeO)BBB(2,4,6-triMeO), (2,4-di MeO)BB(2,5-di MeO)B(2,4-di MeO), (2,4,6-triMeO) BB(2,5-diMeO)B(2,4,6-triMeO), (2,4,6-triMeO)BBB (CN), (2,4,6-triMeO)BBB($NO_2$), ($O_2N$)B(2(1-phenyl)) B(2(1-phenyl))B($NO_2$), (NC)B(2(1-phenyl))B(2(1-phenyl))B(CN), (NC)BBB($NO_2$), ($BrCH_2$)B(2(2-phenyl))B(2(2-phenyl))B($CH_2Br$).

Class BBBB:
—BBBB—, MeBBBBMe, (MeO)BBBB(MeO), (BuO) BBBB(BuO), (HxO)BBBB(HxO), (OcO)BBBB (OcO), (3,4,5-triMeO)BBBB(3,4,5-triMeO).

Class FF:
—FF—, MeFF(CHO).

Class FFF:
—FFF—, MeFFFMe, ($O_2N$)FFF($NO_2$).

Class F(4)F(4)F:
—F(4)F(4)F—.

Class FFFFF:
—FFFFF—, MeFFFFFMe.

Class BF:
—BF—, MeBF—, —BF(CHO), MeBF(CHO), ($O_2N$)BF ($NO_2$), ($NO_2$)BF(CN), ($NO_2$)BF—.

Class BFB:
—BFB—, —BFBMe, MeBFBMe, MeBFNaf, NafFNaf, ($NO_2$)BFB($NO_2$), (2-$NO_2$)BFB(2-$NO_2$), (3-$NO_2$)BFB (3-$NO_2$), (NC) BFB (CN).

Class B(4)B(4)B:
—B(4)B(4)B—.

Class FBF:
—FBF—, —FB(2,5 diMe)F—, —FB(2,5 diEtO)F—, —FAntF—, MeFBFMe, ($O_2N$)FBF($NO_2$)

Class F(4)B(4)F:
—F(4)B(4)F—, —F(4)B(2,6 diMe) (4)F—.

Class BFBF:
—BFBF—.

Class BFBFB:
—BFBFB—, —BFB(2,5-diMeO)FB—, —BFB(2,5-diEtO)FB—, —BFAntFB—, MeBFBFBMe, MeBFB (2,5-di Me)FBMe, MeBFB(2,5-di EtO)FBMe, MeBFB (2,5-di BuO)FBMe, NafFBFNaf.

Class FFBFF:
—FFBFF—, MeFFBFFMe.

Class BTB:
—BTB—, (MeO)BTB(MeO), (3,4,5-triMeO)BTB(3,4,5-triMeO)
Class TBT:
—TBT—, —TB(2,5-diMe)T—.
Class NBN:
—NBN—, (N-methyl)NB(2,5-diOMe)N(N-methyl), (N-methyl)NB(2,5-diOBu)N(N-methyl).

This list is not complete and should not be considered limiting. All other oligomeric conjugated molecules are useful too. Every random combination of aromatic and/or conjugated heterocyclic monomers and/or ethenylene segments with or without various substituents is useful for this application.

The oligomers can be doped to obtain a nominal electrical conductivity. Doping is an oxidation or reduction reaction with incorporation of the dopant to obtain electrical neutrality. Oxidative doping is preferred as the resulting doped oligomers are more stable in air. Doping can be done by adding a dopant to the polymer. Doping can be done in the gaseous phase with a dopant having a sufficient vapor pressure (e.g. $I_2$). When the oligomer is exposed to the $I_2$ vapor, the oxidation reaction can be monitored measuring the electrical resistance. Doping can also be done in a solution of the dopant and a solvent (e.g. $I_2$ in pentane). It is also possible to dope the oligomer before coating in a solution of the oligomer and the dopant and a solvent. A few examples of dopants are: $I_2$, $AsF_5$, $AlCl_3$, $MoOCl_4$, $MoCl_5$, $NO^+$ and $NO_2^+$ salts (e.g. $NOBF_4$, $NOPF_6$, $NOSbF_6$, $NOAsF_6$, $NOCuCl_3$, $NOCH_3SO_3$, $NO_2BF_4$, $NO_2PF6$, $NO_2AsF_6$, $NO_2SbF_6$, $NO_2CF_3SO_3$), $O_2^+AsF_6^-$, $HClO_4$, $HNO_3$, $H_2SO_4$, p-toluenesulfonicacid, benzoylperoxide, $CF_3SO_3H$, $SO_3$, $Br_2$, $(FSO_3)_2$, $FSO_3H$, $Fe(ClO_4)_3$, $FeCl_3$, $Fe(OTs)_3$, $Fe(CF_3SO_3)_3$, Ag salts (e.g. $AgSbF_6$, $AgCF_3SO_3$, AgOTs) leading to doped oligomers with incorporated counterions of the form: $I^-$, $I_3^-$, $I_5^-$, $NO_3^-$, $NO_2^-$, $BF_4^-$, $AsF_5^-$, $PF_6^-$, $Cl^-$, $Br^-$, $SbF_6^-$, $MoOCl_4^-$, $MoCl_6^-$, $FeCl_4^-$, $FeCl_2^-$, $FSO_3^-$, $SO_3^-$, $C_6H_5CO_2^-$, $OTs^-$, $AsF_6^-$, $Br_3^-$, $Br_5^-$, $CF_3SO_3^-$, $CF_3CO_2^-$, $HSO_4^-$.

The oligomers can also be doped by electrochemical doping. The oligomer coating can be oxidized at the anode of an electrochemical cell or reduced at the cathode. Electrochemical exchange of the counterions is also possible. Following dopants can be easily used for electrochemical doping: electrolytes giving the anionic counterions $BF_4^-$, $NO_3^-$, $NO_2^-$, $F^-$, $Cl^-$, $Br^-$, $I^-$, $ClO_4^-$, $ClO_3^-$, $BrO_3^-$, $FeCl_4^-$, $FeCl_2^-$, $CF_3CO_2^-$, $MoOCl_4^-$; $MoCl_6^-$, $AlCl_4^-$, $KS_2O_8^-$, $PF_6^-$, $SbF_6^-$, $HSO_4^-$ $CF_3SO_3^-$, $CH_3SO_3^-$, $CH_3CO_2^-$, $CH_3C_6H_4SO_3^-$, and electrolytes giving the cationic counterions: $NO^+$, $NO_2^+$. The oligomers can be blended with each other or with polymers. A few examples of polymers for blending are: polyacrylonitrile, polyvinylchloride, polymethylmethacrylate, polyvinylidenechloride, polyethyleneoxide, polystyrene, polycarbonate, nylon, celullose-acetate-butyrate, polypropylene, polyethylene, celullose-acetate, polyphenyleneoxide, polyisobutylene, phenylmethyldiphenylsiloxane copolymers, polybis (cyanopropyl), siloxane, polyethyleneimine, polyethylenemaleate, fluoropolyol.

Blending with polymers gives more mechanical strength and stability to the doped oligomer. The polymers can co-operate in the partial selectivity of the coatings. Components other than polymers can be used to enhance the mechanical stability and/or the permeability for gases and liquids, the miscibility, solubility, ability to form dispersions: e.g. graphite, fibers, clays, sand, glass.

For conductimetric gas sensors:
The oligomers or blends with oligomers can be coated before or after doping on a substrate that is provided with electrically conductive contacts (e.g. made of gold), giving by preference an ohmic contact with the coating, and permitting measurement of the electrical resistance over the coating. Electrodes can also be deposited after coating (on top). Electrochemical doping and coating of the film can also be done simultaneously.

For amperometric or voltametric sensors for the liquid phase:
Analogously, the coating, can be made on a glassy carbon electrode.

For coating, spin-coating or spray-coating techniques can be used. Vacuum deposition of the pure oligomer, electrodeposition and dip-coating are also options. Spray-coating is preferred because of the ability to use free-standing metal masks to coat different coatings on a small scale next to each other. The thickness of the coating is optional and can be used to adjust the characteristics of the coating (e.g. the nominal electrical resistance for the application in gas sensors, average response times, environmental stability, expected lifetime, magnitude of the responses, partial selectivity). Layer thickness is in the range of a few nanometers to tenths of a millimeter.

For the construction of chemiresistors for gases, a silicium, alumina or quartz wafer can serve as a substrate. Many dimensions and shapes of the electrodes are possible (e.g. two rectangular shaped electrodes, with a gap of 0.25 millimeter and a length of 1 millimeter).

Advantages that make the use of oligomers advantageous are numerous.

Used in electrodes for electrochemical detection in chromatography, a blended coating is mechanically very stable, and coated electrodes have a good signal to noise ratio for potentiometric and amperometric detectors. The fact that the choice in oligomer, the dopant and the polymer used for blending is virtually unlimited makes the application of these coatings very promising.

For chemically sensitive chemiresistors and their use in an electronic nose, the fact that the use of these coatings gives the possibility to make a whole set of new sensor materials is a first advantage of the invention in the concept of an electronic nose. The resulting sensors have good characteristics.

The typical magnitude of the responses, being the percent fractional resistance change after one minute is maximum 10% for the type 5 sensors of the state of the art (e.g. polypyrrole sensors). For the coatings according to the invention, those responses are generally much higher (e.g. a sensor with a coating 1,4-bis(2-[3,4,5-trimethoxyphenyl] ethenyl)-2,5-dimethoxybenzene gives a response of 45% to acetone relative to dry air).

The sensors according to the invention work at temperatures near room temperature, in opposition to the sensors of type 1 that work at high temperatures. This results in an advantageous low power consumption.

The construction of gas sensors with oligomers in the coating is at least as simple as the construction of type 5 sensors.

Response time can be kept short: firstly because the diffusion in the coating is generally fast and secondly because there is no need to wait for an equilibrium situation to get a useful signal (because of the magnitude of the responses). For instance, a sensor with 1,4-bis(2-[3,4,5-trimethoxyphenyl]ethenyl)-2,5-dimethoxybenzene coating has reached 95% of its maximal response in less than 30 seconds (measured for nine different vapors).

The oligomers can be used as an alternative for graphite in type 4 sensors. The oligomers and blends thereof can also be used as an alternative for the polymers in type 2 and 3 sensors.

The conductimetric detection mechanism can be combined with the detection in type 2 sensors on the same coating.

For sensors in the concept of an electronic tongue, the performance of the materials in the use as a chemically active layer for potentiometric and amperometric and conductimetric sensors indicates a great potential application in the concept of an electronic tongue.

For coupling of the electronic nose or tongue with chromatographic techniques, the performance of the materials in the use as a chemically active layer for potentiometric and amperometric and conductimetric sensors and their great potential in application in the concept of an electronic tongue and an electronic nose open the possibility to use them in new hyphenated techniques like GC/electronic nose and HPLC/electronic tongue.

EXAMPLES

Examples Concerning the Gaseous Phase

1. Apparatus for Measuring the Characteristics According to the Invention

In FIG. 1, one can see an apparatus suitable for testing sensors for gaseous phase analysis.

From a cylinder (10) of industrial grade air a continuous gas stream is generated, which is split into a carrier gas stream (11) and a reference gas stream (12). The flowrates of both are independently controlled by two massflow controllers (mf1 (13) and mf2 (14); Brooks model 5850T). The controllers are regulated by a master controller (Brooks model 5876) to which both massflow controllers are connected. A massflow controller heats up the incoming gas stream with a filament. This generates a temperature gradient which is measured. By means of a feedback mechanism the opening through which the gas stream comes in can be widened or narrowed. The readout on the master controller is digital and shows the rate in percentage of the maximum flowrate. The inventors have established for this experimental setup that there is a linear relation between controller readout (%) and flowrate. The flowrate of the reference stream can be set between 5 and 230 ml/min and that of the carrier stream between 0 and 120 ml/min. Vessels containing compounds to be detected are kept at 15/C by means of thermostatic bath (17). This setup thus enables us to generate vapors with constant, yet material dependent concentrations during all of the experiments. The carrier gas is bubbled through one of the vessels and a saturated vapor results.

By manipulating two three-way valves (twv1 (15) and twv2 (16)) either reference or carrier gas can be sent over the organic films. The valves also enable us to mix the two gas streams and thus we can generate vapor concentrations between 0 g/cm$^3$ and the theoretical concentration of saturation. In a second phase of the research the entire setup was automated and both three-way valves were replaced with computer controlled valves—one two-position and one twelve-position valve (Valco Instruments). Selection of the vapor and its dilution are controlled by these valves and the software application under TestPoint.

In between measurements the dry reference stream (12) is sent over the sensors (18) to prevent contamination from the surrounding air.

The substrate with one or multiple oligomer film(s) deposited on it is plugged into a connector connected to a digital multimeter (19) (dmm) (Keithly model 199). The multimeter measures the electrical resistance between two gold electrodes at a distance of 200 $\mu$m; because it can simultaneously scan eight channels, the substrate is divided into four groups of sixteen contacts i.e. 8 measuring points. This will enables us to deposit 32 different electrically conducting oligomers on the substrate in the future. The range of the digital multimeter lies between 0 Ohm and 300 MOhm; the resolution of the measurements is $33.10^{-4}$%. The delay necessary to switch between channels is 0,4 seconds depending on the difference in magnitude between two consecutive measurements.

A personal computer (80486) (20) collects the data via a RS232-connector. The TestPoint program regulates the multimeters switching between channels and the construction of the graphical representation of the measured values. Any further data manipulations are performed in Microsoft Excel 5.0.

The temperature of the substrate is maintained at a constant 35/C using a second thermostatic bath (tb2) (21). It has been established that at higher temperatures the conductivity of the species drops while at lower temperatures danger exists of condensation of the vapors.

The sensor is covered by a Teflon box. The gas is introduced into this little chamber via tubing. The dead volume of the chamber is only 3 cm$^3$ and thus delays in response due to the filling of the chamber are minimal since the flow is always 100 ml/min. The time between the introduction of the vapor and the moment at which saturation is reached, is estimated to be 6 seconds.

Next, dry reference gas is sent over the film during a certain period, this because during this conditioning the base resistance will rise 2 or 3%, probably due to slight dedoping.

Consequently, the compounds can be consecutively mixed with the carrier gas and every five minutes one of the vapors can be sent over the substrate for one minute. After the experiment the sensor is conditioned again during a certain period of time to remove contaminants from previous experiments. The compounds from a series of compounds are chosen randomly to avoid systematic errors.

2. Examples of Manufacturing Sensors According to the Invention

Example 1: a conductimetric gas sensor based on the trimer 1,4-bis-(2-[3,4,5-trimethoxyphenyl]ethenyl)-2,5-dimethoxybenzene. 0.07 g (0,134 mM) 1,4-bis(2-[3,4,5-trimethoxyphenyl]ethenyl)-2,5-dimethoxybenzene was dissolved in 10 ml of dichloromethane (CH$_2$Cl$_2$). Then we add 10 ml of a saturated iodine/dichloromethane solution. We observe an instantaneous oxidation of the oligomer, as we can see in the change of color from the neutral yellow 1,4-bis(2-[3,4,5-trimethoxyphenyl]ethenyl)-2,5-dimethoxybenzene, to an almost black oxidized form.

On this substance, we deposit a film with the spin coating technique on an alumina substrate. The thickness of the film on this substrate, or on an analogous coated glass plate, can be measured with a Dektak 3030 profilometer.

Example 2: a conductimetric gas sensor based on the trimer 1,4-bis(2-[3,4,5-trimethoxyphenyl]ethenyl)benzene blended with polycarbonate. 0.0793 g 1,4-bis(2-[3,4,5-trimethoxyphenyl]ethenyl) benzene was dissolved in 10 ml of a saturated iodine/dichloromethane solution. One can observe an instantaneous oxidation of the oligomer, the original yellow color turned into purple-black (oxidized form, electrically conducting form). Afterwards, 10 ml of a 5% (g/g) polycarbonate/dichloromethane mixture has been added under continuous stirring. A film was deposited by spraying 2 ml of this mixture on the alumina substrate. On top of this first layer, a second ultra thin layer was deposited using a mixture of 5% (g/g) polycarbonate/dichloromethane with the same technique. Afterwards, this substrate with its two layers was maintained at a temperature of 160° C. ($T_g$ polycarbonate=150° C.) for 5 minutes. The materials are deposited on the electrodes using a metal mask, thus making individual sensors on the substrate, with the spray coating technique.

The substrate is then cooled to room temperature.

Example 3: a conductimetric gas sensor based on a mixture of oligomers: bi[5,5'-(1,2-bis(3-methoxy-2-thienyl)ethene)diyl], ter[5,5'-(1,2-bis(3-methoxy-2-thienyl)ethene)diyl] and quater[5,5¹-(1,2-bis(3-methoxy-2-thienyl)ethene)diyl]. 0.5 g of this mixture was dissolved in 40 ml of dichloromethane and then deposited using the spray technique on a preheated (40° C.) substrate. Doping was done with iodine in the gas phase by putting a pellet of iodine onto the sensors, and shielding it from the environment using a glass bulb.

Example 4: a conductimetric gas sensor based on electrochemically doped 1,4-bis(2-[3,4,5-trimethoxyphenyl]ethenyl)-2,5-dimethoxybenzene with perchlorate ($ClO_4^-$).

The electrochemical doping was done by submerging the substrate into an electrolyte solution (e.g. 1% (v/v) perchlorate acetonitrile) while applying a voltage of 1.7 V. This way, a fast doping reaction is obtained.

3. Examples of Use of Sensors According to the Invention

An experimental setup as described in hereabove (apparatus for measuring the characteristics according to the invention) was used.

During the experiments nine different compounds were used: water (1), methanol (2), ethanol (3), propanol (4), acetone (5), diethyl ether (6), acetic acid (7), ethyl acetate (8) and toluene (9). These were all chosen for a number of reasons: it is easy to generate saturated vapors of these compounds and, since they are frequently used by other research groups, they enable us to compare the results.

Table 1 lists concentrations of the vapors at 15/C; these values have been taken from *Handbook of Chemistry* and *Physics*, Chemical Rubber Company, and to compounds marked with #, 5% (v/v) water has been added to compensate for their hygroscopic properties.

TABLE 1

List of the nine compounds in the experiments with respective vapor pressure and concentration at saturation.

| Number | product | partial vapour pressure at 15/C | concentration in volume % | concentration in gram/m³ |
|---|---|---|---|---|
| 1 | water | 12.8 mm Hg | 1.7% v/v | 13.6 g/m³ |
| 2 | methanol # | 67.2 mm Hg | 8.8% v/v | 125.6 g/m³ |
| 3 | ethanol # | 30.8 mm Hg | 4.1% v/v | 84.1 g/m³ |
| 4 | n-propanol # | 10.7 mm Hg | 1.4% v/v | 36.2 g/m³ |
| 5 | acetone | 127.8 mm Hg | 16.8% v/v | 434 g/m³ |
| 6 | ether # | 306.7 mm Hg | 40.4% v/v | 1334 g/m³ |
| 7 | acetic acid # | 8.8 mm Hg | 1.2% v/v | 31.4 g/m³ |
| 8 | ethyl acetate # | 50.5 mm Hg | 6.6% v/v | 212 g/m³ |
| 9 | toluene | 16.2 mm Hg | 2.1% v/v | 86.2 g/m³ |

Results for the Sensor According to Example 1

Figure 2:
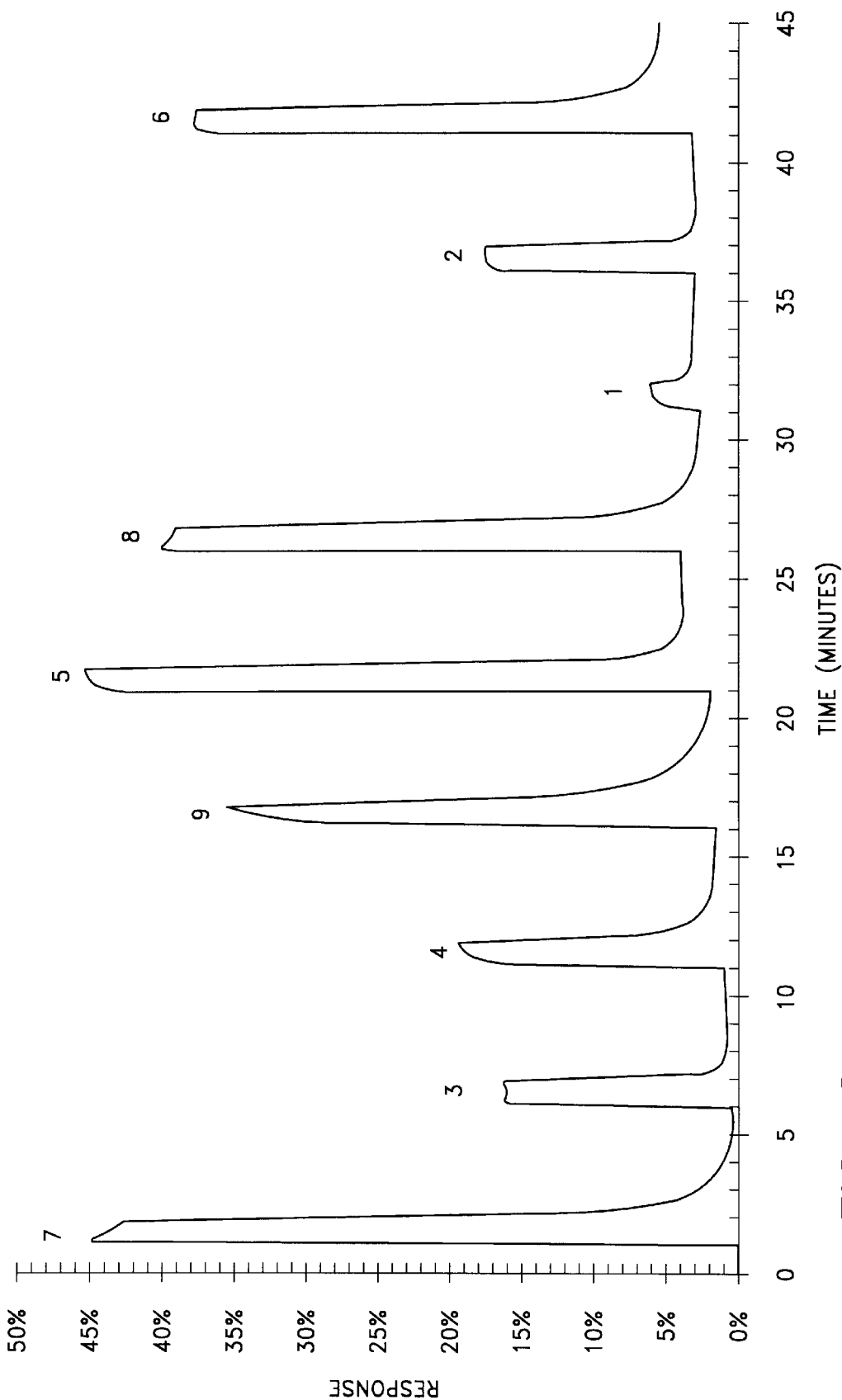
FIG. 2 describes a typical result for example 1.

A typical result is shown in FIG. 2. Product numbers are listed in Table 1. Notice the large range in the ordinate. As is mentioned above, the responses of the gas sensors according to the invention to several gases are generally much higher than any other existing gas sensors (e.g. up to 50%).

These measurements are reproducible. Product numbers are listed in Table 1. We have summarized 10 measurements in Table 2. The initial resistance is 26,5 kΩ. The response % R is expressed in percentages and has been defined as in Equation 1. In this equation, $R_i$ is the initial resistance and $R_f$ is the resistance after exposure to a defined gas during a certain time (e.g. one minute). In Table 2 stands stdev for the standard deviation on the results and is also expressed in percentages. definition of response: % $R=(R_f-R_i)\times 100\%/R_i$

TABLE 2 results of 10 measurements as described in example 1.

| | water | methanol | ethanol | propanol | toluene | ethyl acetate | acetone | acetic acid | ether |
|---|---|---|---|---|---|---|---|---|---|
| % R | 3.09 | 15.32 | 16.04 | 18.07 | 36.66 | 36.06 | 45.13 | 42.25 | 36.64 |
| st dev | 0.683 | 0.992 | 2.050 | 1.832 | 3.145 | 2.721 | 3.431 | 3.981 | 1.917 |

Notice that the response time (the time required to reach 95% of the maximum response) is about 6 to 12 seconds.

Results for the Sensor According to Example 2

Figure 3:
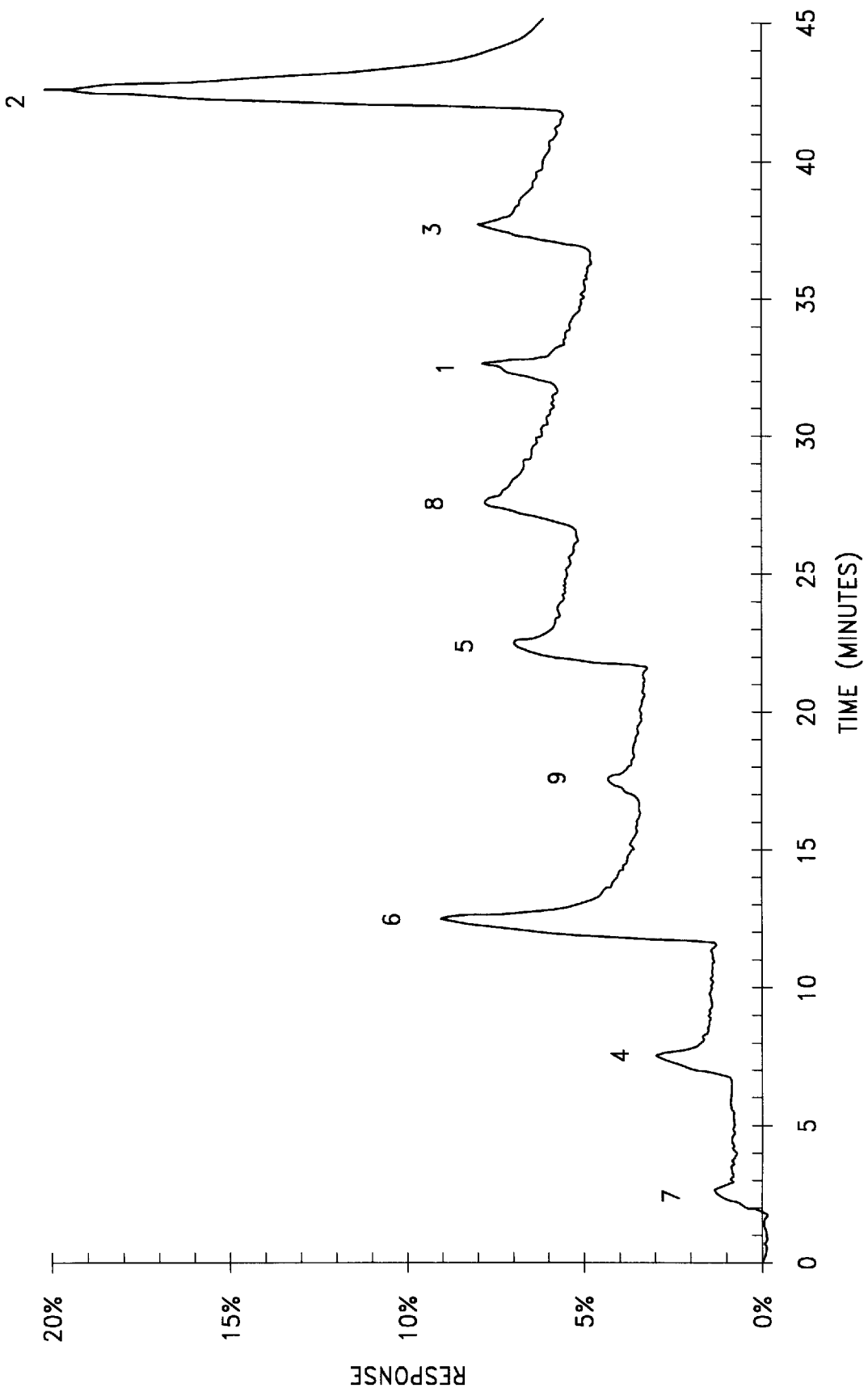
FIG. 3 describes a typical result for example 2.

A typical result is shown in FIG. 3.

Product numbers are listed in Table 1. We have summarized 10 measurements on this kind of sensors in Table 3. % R is defined as in example 1.

TABLE 3 results of 10 measurements as described in example 2.

|  | water | methanol | ethanol | propanol | toluene | ethyl acetate | acetone | acetic acid | ether |
|---|---|---|---|---|---|---|---|---|---|
| % R | 1.82 | 17.54 | 3.31 | 2.11 | 0.92 | 2.65 | 4.02 | 1.45 | 8.12 |

Figure 4:
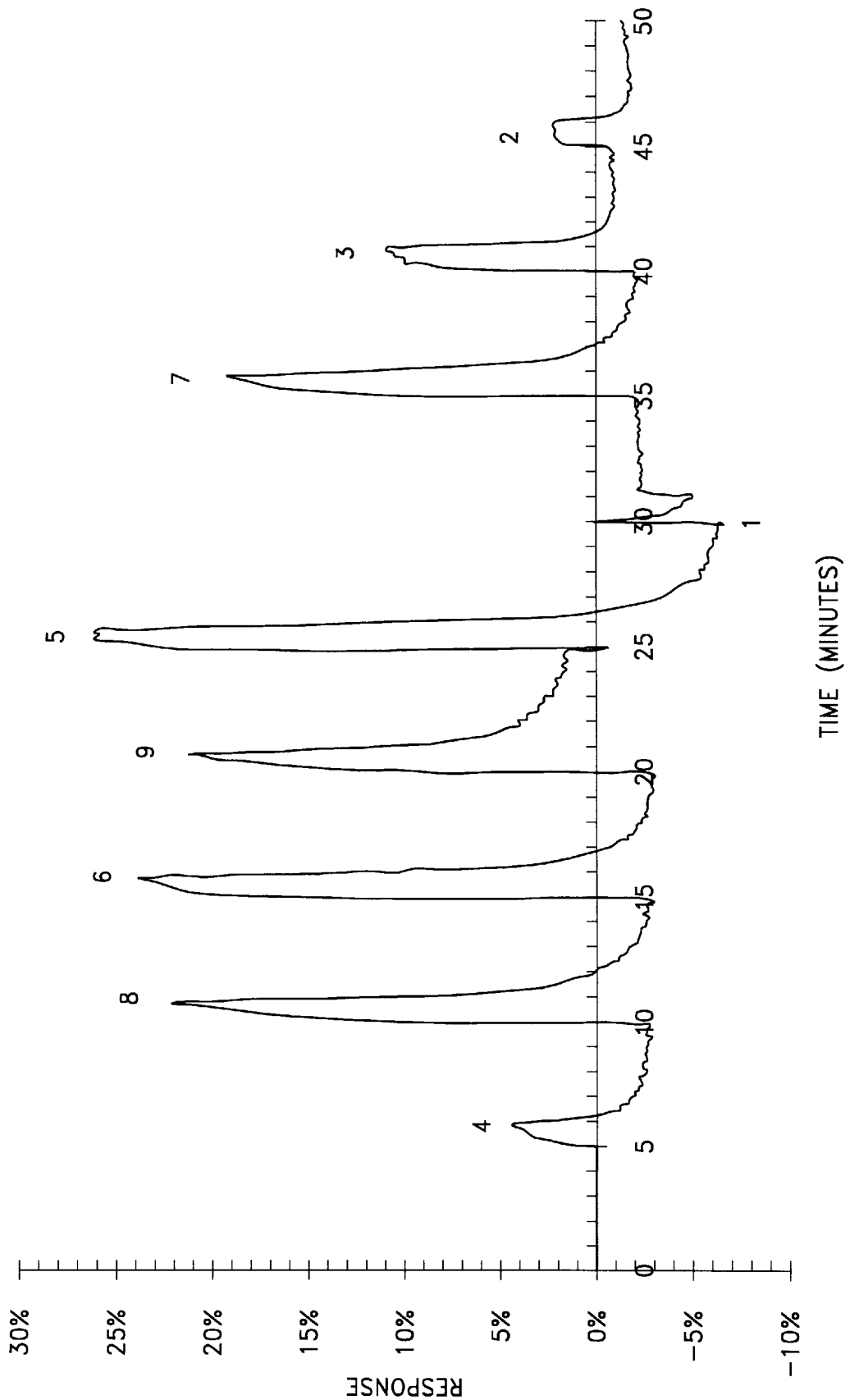
FIG. 4 describes a typical result for example 3.

Results for the Sensor According to Example 3
A typical result can be seen in FIG. 4.

TABLE 4 results of a typical measurement as described in example 3.

|  | water | methanol | ethanol | propanol | toluene | ethyl acetate | acetone | acetic acid | ether |
|---|---|---|---|---|---|---|---|---|---|
| % R | −3.9 | 0.8 | 5.6 | 3.8 | 12.2 | 17.3 | 16.6 | 13.7 | 11.8 |

Figure 5:
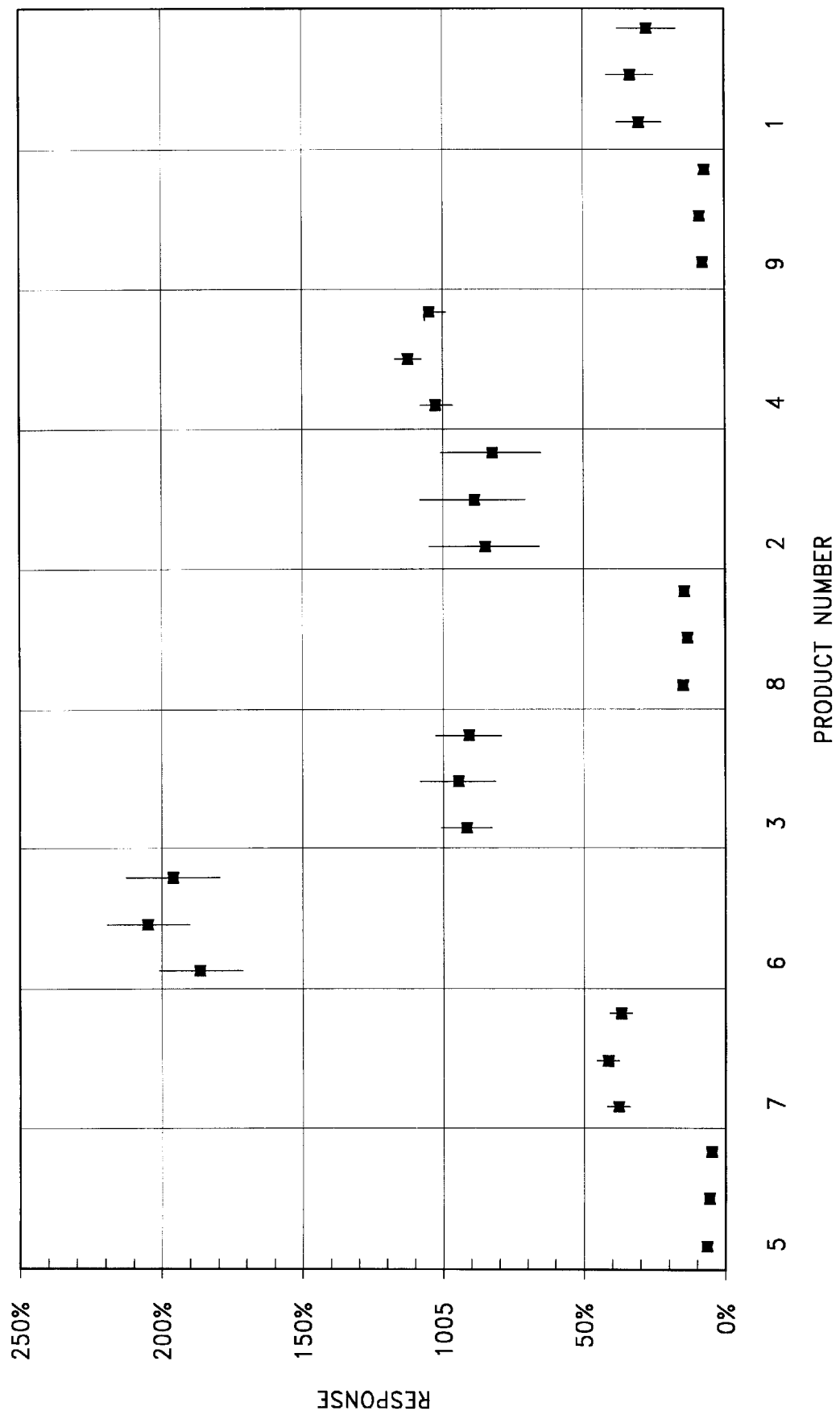
FIG. 5 describes the average results for 3 analogue sensors after 7 measurements.

Results for the Sensor According to Example 4
In FIG. 5, the results of 3 identical sensors (same product, same thickness) are displayed.

The standard procedure to test the sensory properties of these sensors has been repeated 5 times within 7 hours.

The average response is shown, product numbers are listed in Table 1, and the error-lines are calculated as follows:

% R=$\mu \pm \sigma$
$\mu$=average response
$\sigma$=standard deviation

TABLE 5 results of 7 measurements as described in example 4.

|  | water | methanol | ethanol | propanol | toluene | ethyl acetate | acetone | acetic acid | ether |
|---|---|---|---|---|---|---|---|---|---|
| % R | 30.97 | 86.83 | 93.67 | 107.6 | 8.68 | 14.94 | 5.97 | 39.44 | 196.6 |
| st dev | 8.83 | 18.34 | 11.05 | 4.54 | 0.82 | 1.93 | 0.56 | 3.60 | 15.33 |

Summary of the Results for the Sensors According to Examples 1 to 4

Figure 6:
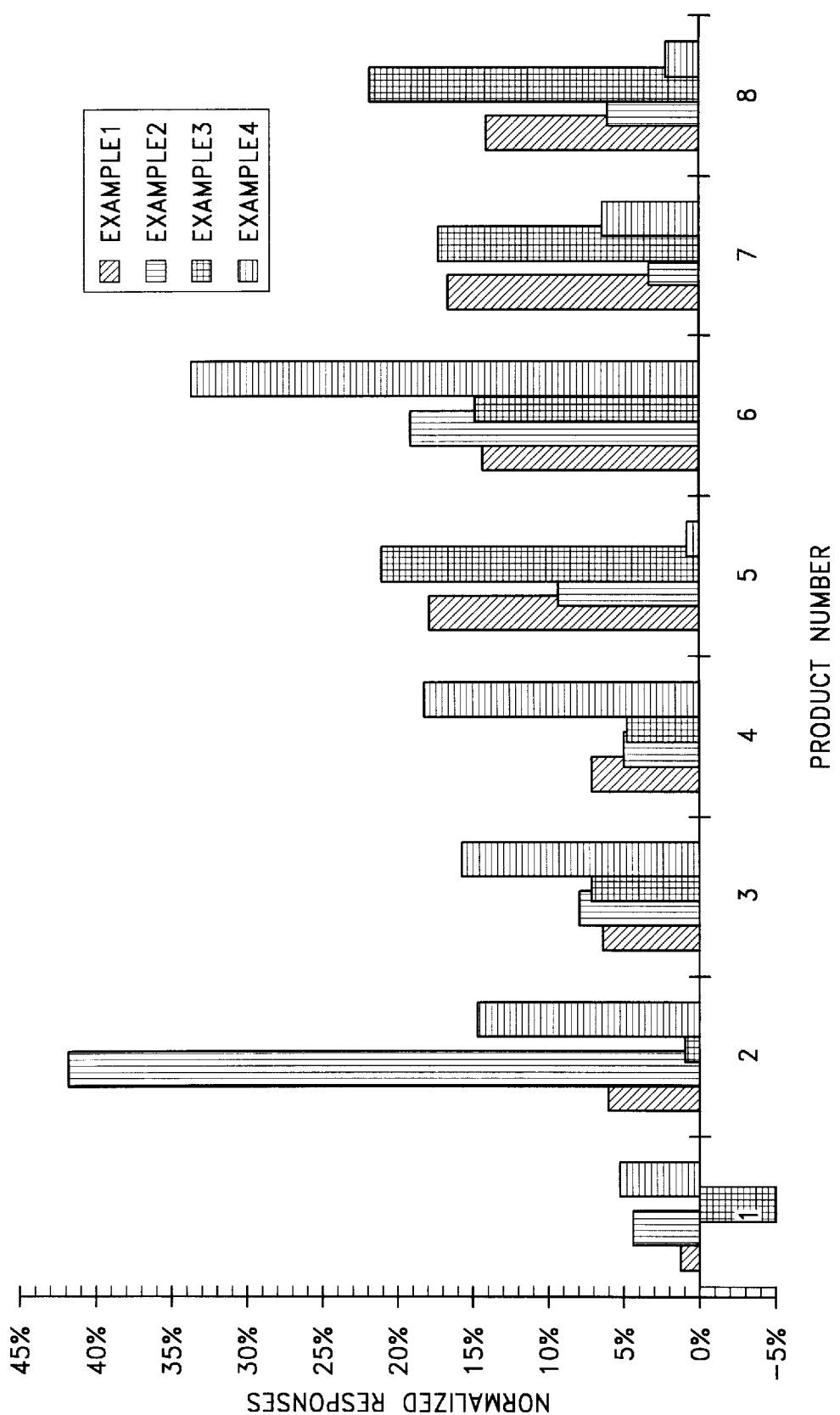
FIG. 6 describes a summary of examples 1 to 4.

Comparing the results of examples 1 to 4 (FIG. 6) one can see that all the sensors give a response to all gases, but that every sensor reacts differently for a given gas. This is called the partial selectivity of a sensor-array. Thus, the product as in example 2 is a good methanol-sensor, and the sensor as in example 4 is a good alcohol sensor. Combining the information from these 4 sensors, allows us to detect the components in the gas mixture.

As one can see, the more different sensors one can make, the bigger the differentiation will be. This is one of the main advantages using oligomers, besides the large responses: the number of different oligomers is virtually unlimited. Chemical modifications can be done, which allows us to introduce for example other substituents. Therefore, these products as described above are good candidate-sensors for an electronic nose.

It is obvious that a number of changes and modifications can be done without deviating from the concept of this invention.

Examples of the Applications in Liquid Phase
Fabrication of a Potentiometric Measuring Cell The analytes are sprayed directly onto the surface of the working electrode. The potential over the membrane is measured by monitoring the potential between the working (31) and the reference electrode (30). The coated electrode shows excellent response times (less then 1s) and no memory effects were found.

Figure 8:
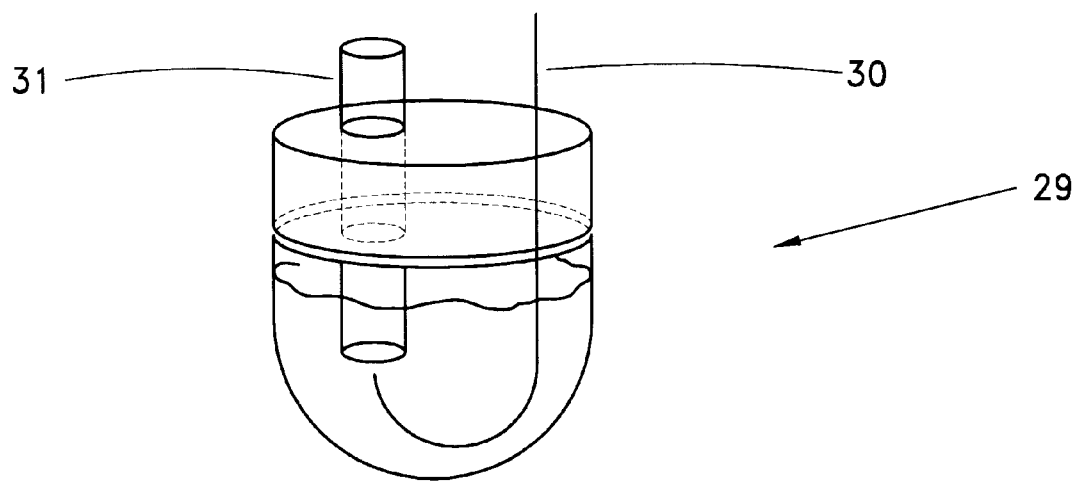
FIG. 8 describes the setup for a potentiometric measuring cell.

The setup of a potentiometric measuring cell (29) is shown in FIG. 8. It uses a large glass container in which the working (31) and the reference electrodes (30) are placed. This type of cell is called a large volume wall-jet. The working electrode (31) consists of a glassy carbon electrode spraycoated with the conducting blend. The outlet of the chromatographic system is placed at a distance of approximately 100 $\mu$m of the surface of the working electrode.

Use of the Material in Potentiometric Detectors Example 5

Figure 7:
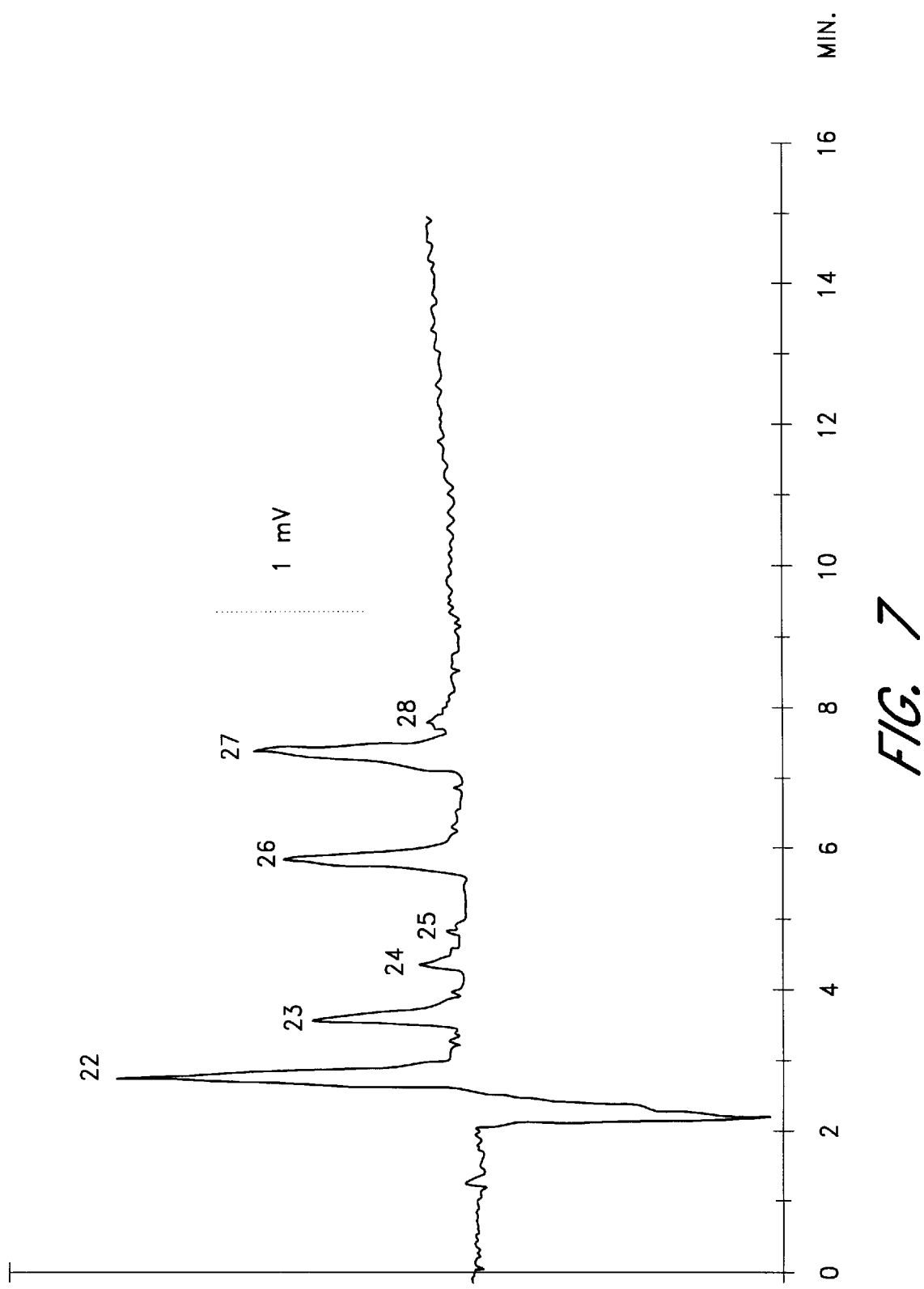
FIG. 7 describes a typical result for example 5.

An example of use and performance of the material as a potentiometric sensor in HPLC analysis is shown in FIG. 7. This is an LC separation of organic acids; tartaric acid (22), maleic acid (23), lactic acid (24), acetic acid (25), citric acid (26), fumaric acid (27) and succinic acid (28). The chromatographic column was a Merck (Darmstadt, FRG) RP C 18 column, particle size 5 $\mu$m, internal diameter 4 mm, length 10 cm. The acids were eluted using 1 mM $H_3PO_4$ solution at a flow rate of 0.5 ml/min. 50 ml of a $10^{-4}$ M solution of the acids in 1 mM $H_3PO_4$ was injected.

The figure shows that organic acids can be detected sensitively using the new electrode material. Organic acids are normally detected using UV detection, having the same sensitivity as the potentiometric method. UV detection however is less selective than potentiometry. Analysis of complex food or biological mixtures by UV detection gives rise to interferences causing difficult detection of the acids.

Coating of Electrodes

Figure 10:
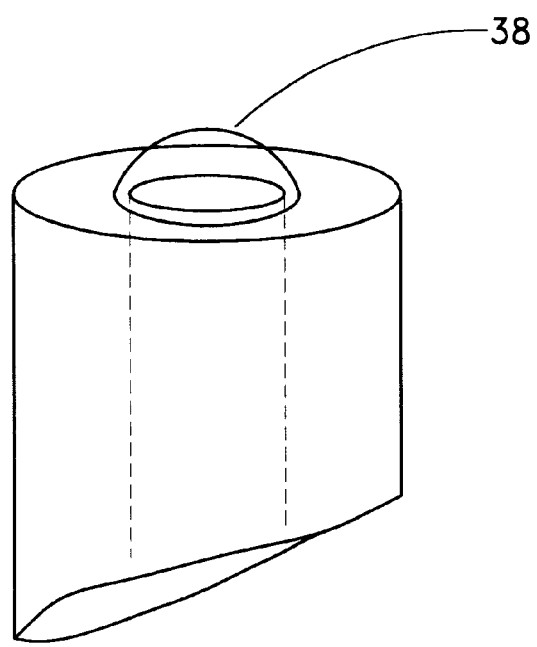
FIG. 10 describes the setup for an amperometric electrode.

The electrodes are coated by applying a droplet (38) of a solution containing the polymer, the conducting component and $I_2$ as the dopant (FIG. 10). The solvent is evaporated under atmospheric conditions, the thickness of the film is approximately 25 μm. The coated electrodes show good mechanical and chemical stability. The material can be modified chemically to make it possible to attach enzymes at the surface.

Use of the Material in Amperometric Detectors.

The material can also be used in amperometric detectors. The setup used for this kind of experiment is identical to that used for potentiometry. Three electrodes are used instead of two (a working, a reference and a counter electrode). The working electrode again is coated with the conducting blend.

Figure 9:
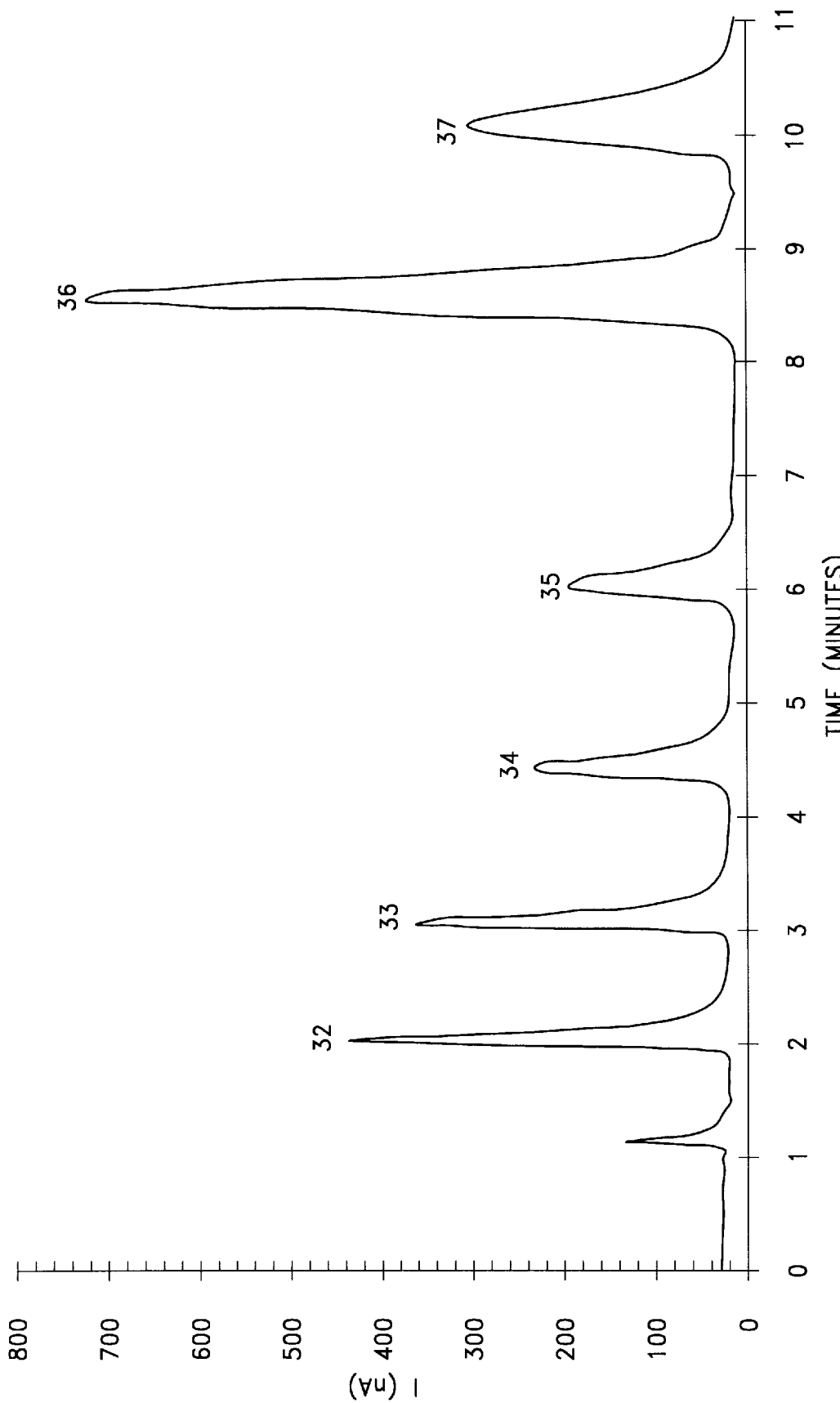
FIG. 9 describes a chromatogram of 6 catecholamines, detected with an amperometric sensor according to the invention.

FIG. 9 shows a chromatogram of six catecholamines. FIG. 9: chromatogram of six catecholamines detected amperometicaly, dl-4-hydroxy-3-methoxy mandelic acid (A) (32), norepinephrine (B) (33), epinephrine (C) (34), 3,4-dihydroxybenzylamine (D) (35), 3,4-dihydroxyphenylacetic acid (E) (36) and dopamine (F) (37) using a RP C18 (5 mm) column, ID 4.6 mm and length 10 cm. The analytes were eluted using a 0.1 mM phosphate buffer (pH 3.8) with 5 mM EDTA and 5% methanol at a flow rate of 1 ml/min.

What is claimed is:

1. A chemically sensitive sensor for the detection of an analyte in a fluid comprising:
   a chemically sensitive probe consisting essentially of at least one arylene alkenylene oligomer, wherein at least one response signal is determined by said oligomer; and
   means for converting said response signal to a sensor response.

2. The sensor as recited in claim 1, wherein said response signal is determined by the interaction of said oligomer with said analyte.

3. The sensor as recited in claim 1, wherein said signal is determined by the interaction of said oligomer with said fluid.

4. A chemically sensitive sensor as recited in claim 1, wherein said fluid is a liquid.

5. A chemically sensitive sensor as recited in claim 1, wherein said fluid is a gas.

6. A chemically sensitive sensor as recited in claim 1, wherein said fluid is a vapor.

7. A chemically sensitive sensor as recited in claim 1, wherein said sensor further comprises a carrier, said probe being a coating on the carrier surface.

8. A chemically sensitive sensor as recited in claim 7, wherein said probe forms a film, said film having a thickness being in the range of about 1 nm to 0.5 mm.

9. A chemically sensitive sensor as recited in claim 7, wherein said arylene alkylene oligomer is coated on said carrier surface by a coating technique chosen from the group consisting of spin-coating, spray-coating, dip-coating, vacuum deposition and electro-deposition.

10. A chemically sensitive sensor as recited in claim 1, wherein said sensor further comprises electrodes able to put a voltage over said chemically sensitive probe.

11. A chemically sensitive sensor as recited in claim 1, wherein said arylene alkenylene oligomers comprise a number of aromatic and/or heteroaromatic residues, said number being in the range of 2 to 20.

12. A chemically sensitive sensor as recited in claim 11, wherein said aromatic and/or heteroaromatic residues are chosen from the group consisting of benzene, pyrrole, thiophene, naphthalene, anthracene, bithienyl, aniline and indole.

13. A chemically sensitive sensor as recited in claim 11, wherein said aromatic and/or heteroaromatic residues are connected by one or more alkenyl segments.

14. A chemically sensitive sensor as recited in claim 13, wherein said aromatic and/or heteroaromatic residues and/or said alkenyl segments are substituted with one or more substituents chosen from the group consisting of all alkyl groups, all alkoxy groups, —CHO, —CN, —COOH, $C_6H_5$, anthracene, naphthalene and —$CH_2X$ and —X with X chosen from the group consisting of F, Cl, Br and I.

15. A chemically sensitive sensor as recited in claim 1, wherein said arylene alkenylene oligomer is doped with one or several dopants, thereby changing the resistance of said oligomer.

16. A chemically sensitive sensor as recited in claim 15, wherein the doping is oxidative or reductive.

17. A chemically sensitive sensor as recited in claim 15, wherein the doping is chemical or electrochemical.

18. A chemically sensitive sensor as recited in claim 15, wherein said dopant is advantageously chosen from the group consisting of $I_2$, $AsF_5$, $AlCl_3$, $MoOCl_4$, $MoCl_5$, $NO^+$ and $NO_2^+$ salts, $O_2^+AsF_6^-$, $HClO_4$, $HNO_3$, $H_2SO_4$, p-toluenesulfonicacid, benzoylperoxide, $CF_3SO_3H$, $SO_3$, $Br_2$, $(FSO_3)_2$, $FSO_3H$, $Fe(ClO_4)_3$, $FeCl_3$, $Fe(OTs)_3$, $Fe(CF_3SO_3)_3$, Ag salts leading to doped oligomers with incorporated counterions of the form chosen from the group consisting of $I^-$, $I_3^-$, $I_5^-$, $NO_3^-$, $NO_2^-$, $BF_4^-$, $AsF_5^-$, $PF_6^-$, $Cl^-$, $Br^-$, $SbF_6^-$, $MoCl_4^-$, $MoCl_6^-$, $MoCl_6^-$, $FeCl_4^-$, $FeCl_2^-$, $FSO_3^-$, $SO_3^-$—, $C_6H_5CO_2^-$, $OTs^-$, $AsF_6^-$—, $Br_3^-$, $Br_5^-$, $CF_3SO_3^-$, $CF_3CO_2^-$, and $HSO_4^-$, electrolytes giving the anionic counterions chosen from the group consisting of $BF_4^-$, $NO_3^-$, $NO_2^-$, $F^-$, $Cl^-$, $Br^-$, $I^-$, $ClO_4^-$, $ClO_3^-$, $BrO_3^-$—, $FeCl_4^-$, $FeCl_2^-$, $CF_3CO_2^-$, $MoOCl_4^-$, $MoCl_6^-$, $AlCl_4^-$, $KS_2O_8^-$, $PF_6^-$, $SbF_6^-$, $HSO_4^-$ $CF_3SO_3^-$, $CH_3SO_3^-$, and $CH_3CO_2^-$, $CH_3C_6H_4SO_3^-$, and electrolytes giving the cationic counterions $NO^+$, or $NO_2^+$.

19. A chemically sensitive sensor as recited in claim 1, wherein said arylene alkylene oligomer is blended with one or several polymers.

20. A chemically sensitive sensor as recited in claim 19, wherein said polymers are chosen from the group consisting of polyacrylonitrile, polyvinylchloride, polymethylmethacrylate, polyvinylidenechloride, polyethyleneoxide, polystyrene, polycarbonate, nylon, cellulose-acetate-butyrate, polypropylene, polyethylene, cellulose-acetate, polyphenyleneoxide, polyisobutylene, phenylmethyl-diphenylsiloxane copolymers, polybis (cyanopropyl), siloxane, polyethyleneimine, polyethylenemaleate, and fluoropolyol.

21. An array of chemically sensitive sensors, comprising two or more chemically sensitive sensors as recited in claim 1.

22. Electronic nose for the detection and/or identification of an analyte in gaseous phase solution, comprising an array of chemically sensitive sensors as recited in claim 21 and a sensor response pattern recognition system.

23. Electronic tongue for the detection and/or identification of an analyte in liquid phase solution, comprising an array of chemically sensitive sensors as recited in claim 21 and a sensor response pattern recognition system.

* * * * *

UNITED STATES PATENT AND TRADEMARK OFFICE
CERTIFICATE OF CORRECTION

PATENT NO. : 6,042,788
DATED : March 28, 2000
INVENTOR(S) : Michael De Wit, Emmanuel Vanneste, Frank Blockhuys, Gunter Verreyt, Wim Tachelet, Luc J. Nagels and Herman J. Geise It is certified that error appears in the above-identified patent and that said Letters Patent is hereby corrected as shown below:

Title page,
Item [73], add: -- Universitaire Instelling Antwerpen (UIA) -- as an Assignee.

Signed and Sealed this

Twenty-second Day of October, 2002

*Attest:*

JAMES E. ROGAN
*Attesting Officer — Director of the United States Patent and Trademark Office*